US009816905B2

(12) United States Patent
Colladon

(10) Patent No.: US 9,816,905 B2
(45) Date of Patent: Nov. 14, 2017

(54) METHOD FOR ANALYSING A FRACTURE FACE OF A PART OF A TURBINE ENGINE

(71) Applicant: SNECMA, Paris (FR)

(72) Inventor: Fabrice Colladon, Dammarie-Les-Lys (FR)

(73) Assignee: SNECMA, Paris (FR)

( * ) Notice: Subject to any disclaimer, the term of this patent is extended or adjusted under 35 U.S.C. 154(b) by 112 days.

(21) Appl. No.: 14/785,525

(22) PCT Filed: Apr. 11, 2014

(86) PCT No.: PCT/FR2014/050880
§ 371 (c)(1),
(2) Date: Oct. 19, 2015

(87) PCT Pub. No.: WO2014/174179
PCT Pub. Date: Oct. 30, 2014

(65) Prior Publication Data
US 2016/0061699 A1 Mar. 3, 2016

(30) Foreign Application Priority Data

Apr. 22, 2013 (FR) .................... 13 53660

(51) Int. Cl.
*G01J 3/46* (2006.01)
*G01N 3/06* (2006.01)
(Continued)

(52) U.S. Cl.
CPC .......... *G01N 3/068* (2013.01); *G01M 5/0016* (2013.01); *G01M 5/0033* (2013.01); *G01N 21/25* (2013.01);
(Continued)

(58) Field of Classification Search
CPC ..... G01N 2203/006; G01N 2203/0062; G01N 2203/0064; G01N 2203/0066
See application file for complete search history.

(56) References Cited

U.S. PATENT DOCUMENTS 3,918,299 A * 11/1975 Donnadieu ............ G01N 3/066
324/209
6,970,182 B1 * 11/2005 Schultz ................. G06T 7/0008
348/86
2007/0213942 A1 9/2007 Ponson et al.

FOREIGN PATENT DOCUMENTS

FR         2 968 759 A1    6/2012
WO    WO 2007/048934 A1   5/2007

OTHER PUBLICATIONS

International Search Report dated Jul. 1, 2014, in PCT/FR2014/050880 filed Apr. 11, 2014.
(Continued)

*Primary Examiner* — Abdullahi Nur
(74) *Attorney, Agent, or Firm* — Oblon, McClelland, Maier & Neustadt, L.L.P.

(57) ABSTRACT

Process for analyzing a fracture or crack surface of a TiAl turbomachine part, comprising at least one of the steps consisting in: a) marking on the surface the position and the orientation of cleavage facets, so as to identify a region of fracture or crack initiation and to determine the direction of propagation of this fracture or crack, b) examining the surface and detecting the regions with the presence of equiaxed grains and/or lamellar grains, so as to evaluate the temperature at which the fracture or crack has taken place, and c) comparing the heat tintings of the surface with those of samples from a heat tinting color chart so as to evaluate the speed of propagation of the fracture or crack.

11 Claims, 6 Drawing Sheets

(51) Int. Cl.
  *G01N 33/20*   (2006.01)
  *G01M 5/00*   (2006.01)
  *G06K 9/00*   (2006.01)
  *G01N 21/25*   (2006.01)
  *H01J 37/26*   (2006.01)

(52) U.S. Cl.
  CPC ......... *G01N 33/20* (2013.01); *G06K 9/00147* (2013.01); *H01J 37/26* (2013.01); *G01N 2203/0062* (2013.01); *G01N 2203/0067* (2013.01); *G01N 2203/0226* (2013.01); *G01N 2203/0647* (2013.01)

(56) References Cited

OTHER PUBLICATIONS

Poursaeidi, E. et al., "Failure analysis of generator rotor fan blades", Engineering Failure Analysis, vol. 14, No. 5, (Feb. 9, 2007), pp. 851-860.

Witek, L., "Failure analysis of turbine disc of an aero engine", Engineering Failure Analysis, vol. 13, No. 1, (Jan. 1, 2006), pp. 9-17.

Mazur, Z. et al., "Steam turbine blade failure analysis", Engineering Failure Analysis, vol. 15, (2008), pp. 129-141.

\* cited by examiner

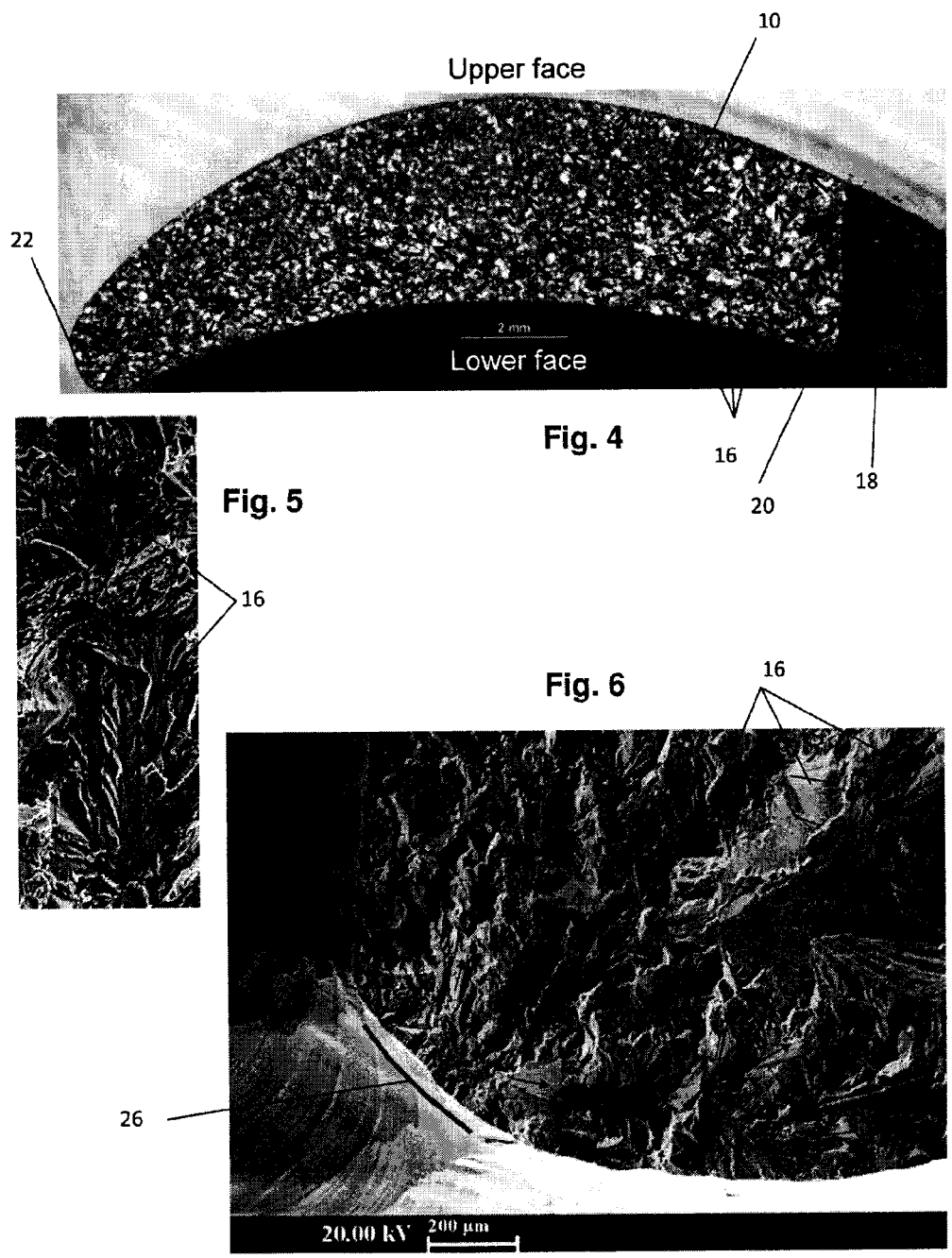

METHOD FOR ANALYSING A FRACTURE FACE OF A PART OF A TURBINE ENGINE

TECHNICAL FIELD

The present invention relates to a method for analysing a fracture or crack face of a metal part of a turbine engine, and in particular made of a TiAl-based metal alloy.

PRIOR ART

Turbine engine parts may crack or fracture in the course of the development thereof or during use. An analysis of the fracture or cracking surface (fractography) referred to as a "face" is thus carried out in a laboratory. This face corresponds to the fracture surface of a part or to the cracking surface before opening in the laboratory for an unbroken cracked part. The analysis of the face should make it possible to explain how and why the parts broke or cracked. The main objectives of this analysis are in particular to locate the initiation region of the crack or fracture, to identify any metallurgical or geometrical peculiarities of the part, to determine the type of crack or fracture (brutal, vibratory or cyclic), the method of loading (bending, twisting or pulling) the part which caused the fracture or crack, etc.

The fracture or crack faces of turbine engine parts made of a nickel or cobalt-based metal alloy can be read and the above-mentioned analysis is carried out without too much difficulty, because said faces are relatively smooth and the fracture or crack initiation regions can be deduced from the shape and the orientation of macroscopic and microscopic fatigue striations which can be seen on the face.

New metal alloys, in particular TiAl-based metal alloys, are used to manufacture parts of a turbine engine, said new alloys being as resistant nickel-based alloys and having the advantage of being lighter. It is necessary to study the behaviour of these new alloys in the event of fracture or cracking.

Bibliographical studies and laboratory experiments (pulling, high cycle fatigue, low cycle fatigue, creep, etc.) indicate that these new alloys do not react in a conventional manner to cracks and fractures, and this makes it very difficult to locate an initiation site of a fracture or crack, the direction of propagation of the fracture or crack and the distinction between a crack progressing with fatigue and a brutal fracture.

In particular when observing the fracture face of a turbine blade made of a TiAl-based alloy (such as Ti48-2-2), it is noted that this face is homogeneous, and that it is very difficult to locate the initiation region of the fracture, the propagation front of said fracture and the type of fracture.

There is thus a real need for a methodology for analysing the face of parts produced from said new metal alloys which is simple, efficient and economical, and can be applied in the field of assessing damage analyses.

SUMMARY OF THE INVENTION

The invention proposes a method for analysing a fracture or crack face of a metal part of a turbine engine, in particular made of extremely fragile fracture material, such as a TiAl-based alloy, said face corresponding to the fracture surface or to the cracking surface before opening in the laboratory for an unbroken cracked part, characterised in that it comprises at least one of the steps consisting in:

a) identifying on the face the position and orientation of cleavage facets so as to identify an initiation region of the fracture or crack and to determine the direction of propagation of said fracture or crack, b) examining the face and detecting the regions where equiaxed grains and/or lamellar grains are present, so as to evaluate the temperature at which the fracture or crack was made, and c) comparing the heat tint(s) of the face with those of samples from a heat tint colour chart, said samples being produced from the same material as the part and being subjected to oxidising heat treatments at predetermined temperatures and for predetermined periods of time, so as to evaluate the speed of propagation of the fracture or crack.

The more steps the method according to the invention comprises, the more complete the analysis of the face of the part is. The method may comprise only step a), only step b), only step c), steps a) and b), steps a) and c), steps b) and c), or steps a), b) and c).

Steps a), b) and/or c) are carried out in any order, but are preferably carried out in the order shown above.

The method according to the invention makes it possible to precisely locate the initiation region of the fracture or crack (step a)), to know the temperature at which the fracture takes place or the crack forms (step b)), and/or to determine whether it is a brutal fracture or a crack progressing with fatigue (step c)).

In the present application, an extremely fragile fracture material is understood to mean a material on which a fracture does not leave any conventional mark which can be analysed to investigate the origin of said fracture.

Step a) is based on analysing the position and the orientation of the cleavage facets of the face. The fragile crystals of the material of the part break along specific planes forming said facets. In general, said facets are all oriented substantially radially towards the outside relative to a central point which is located in the region of the propagation front of the fracture or crack. The facets are distributed over substantially the entire surface of the face which has been fractured or cracked. The final fracture region is generally located opposite the initiation region. The facets thus make it possible to find out the direction of propagation of the fracture or crack.

Step a) is for example carried out using a binocular loupe and/or by means of a scanning electron microscopy (SEM) imaging system. Step a) may consist in identifying and directly tracing, in a video image of the face, the position and orientation of the cleavage facets.

Step a) may further consist in determining at least one geometrical (scratch, impact, etc.) or metallurgical (porosity, inclusion, etc.) fault which is able to explain the appearance of the crack or fracture.

The crack or fracture face is modified according to the temperature at which the fracture or crack was made. The material of the part may comprise equiaxed grains and/or lamellar grains which can be seen on the face. Equiaxed grains do not have a favoured orientation (symmetrical and isotropic crystals) and generally appear when the material is subjected to a temperature which is greater than or equal to 500° C. The presence or absence of said grains on a fracture face thus makes it possible to evaluate the temperature at which the fracture or crack was made. The method may thus consist, in step b), in determining whether the fracture or crack was made above or below 500° C. Step b) may further consist in determining whether the fracture or crack took place when hot during use or when cold during manufacture.

Step b) is for example carried out using a binocular loupe and/or by means of a scanning electron microscopy (SEM) imaging system.

Step b) of the method may consist in evaluating the temperature at which the fracture or crack was made by estimating the density of the equiaxed grains on the face. Indeed, the inventor noted that the density of said grains increases with the temperature.

The method may further consist, in step b), in examining the face and detecting the regions where ductile dimples are present. The TiAl alloy is relatively fragile up to 800° C. because it has an elongation at fracture of 1 to 3%. This elongation increases significantly above 800° C. and is at 20% approximately at 900° C. Above 800° C., ductile dimples appear on the face and can easily be identified by observing an SEM image of the face for example. In the case where such dimples are present on a face, this thus signifies that the part has been subjected to abnormal overheating because said alloy is generally not used at above 800° C. in a turbine engine because it loses mechanical properties. Detecting ductile dimples on a face thus makes it possible to evaluate the temperature to which the part has been subjected.

Step c) makes it possible to determine the type of fracture of the part, by comparing the heat tint(s) of the face with those of a sample from a colour chart or previously prepared chart, as described in the earlier application FRA1-2,968, 759 by the applicant. If the fracture surface of the face has a uniform colour, the fracture was brutal. On the contrary, if the fracture surface has a graduated colour, the fracture was progressive and is generally due to vibratory or oligocyclic fatigue. This type of fatigue is determined by dating stages of propagation of the fracture through heat tint gradients of the face.

In step c), before the samples are subjected to heat treatments, a notch can be made in each sample which is then subjected to stresses to produce a fracture or crack in the region of said notch.

Step c) may further consist in comparing the heat tints on a surface of the part with those of the above-mentioned samples so as to evaluate the temperature level reached by the part.

DESCRIPTION OF THE DRAWINGS

The invention will be better understood, and other details, features and advantages of the invention will become apparent upon reading the following description, given by way of non-limiting example with reference to the accompanying drawings, in which:

FIG. 4 is a binocular loupe image of another fracture face of a TiAl blade, FIG. 5 is an SEM image of part of the face from FIG. 4, FIG. 6 is a partial SEM image of another fracture face of a TiAl blade.

DETAILED DESCRIPTION

Figure 1:
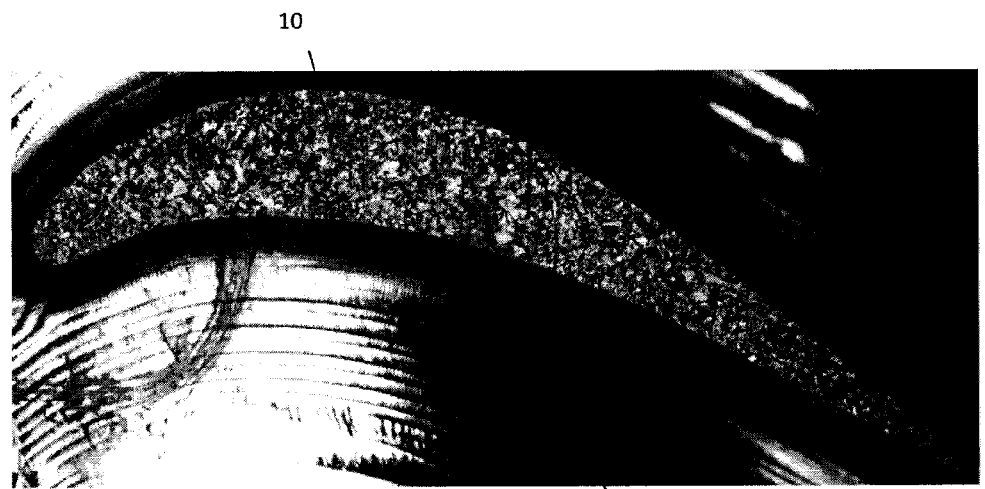
FIG. 1 is a binocular loupe image of a fracture face of a TiAl turbine engine blade.

Reference is firstly made to FIG. 1, which is a binocular loupe image of a fracture face 10 of a TiAl blade 12 of a turbine engine turbine. The fracture face 10 extends in a plane which in this case is transverse to the leaf of the blade.

As explained above, it is noted that the fracture shape of this face is relatively homogeneous, and that currently employed techniques for analysing fracture faces of turbine engine parts cannot be used to analyse this face.

Figure 2:
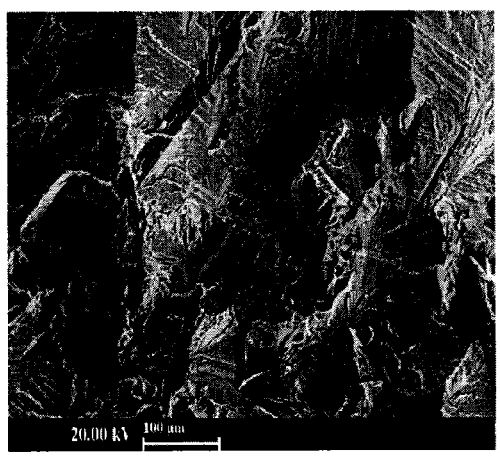
FIGS. 2 and 3 are SEM images of the fracture face of the blade from FIG. 1.
Figure 3:
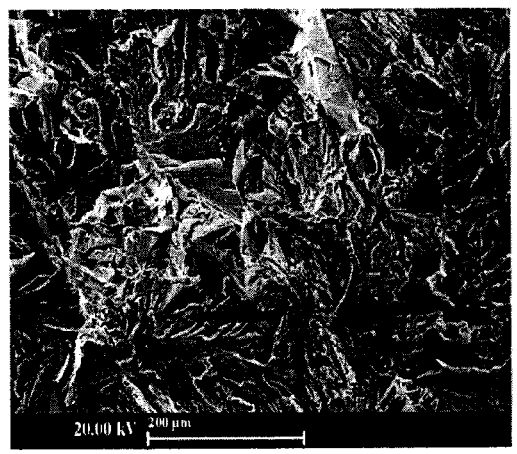

FIGS. 2 and 3 are SEM images of fracture faces of TiAl turbine blades, the fractures having been caused deliberately by fatigue loading. The face in FIG. 2 is a face with a crack from vibratory or polycyclic fatigue (HCF) and that in FIG. 3 is a face with a static fracture. There is a notable lack of difference in fractographic shape between these faces, a similar observation having been made with oligocyclic fatigue (LCF) or creep.

Figure 11:
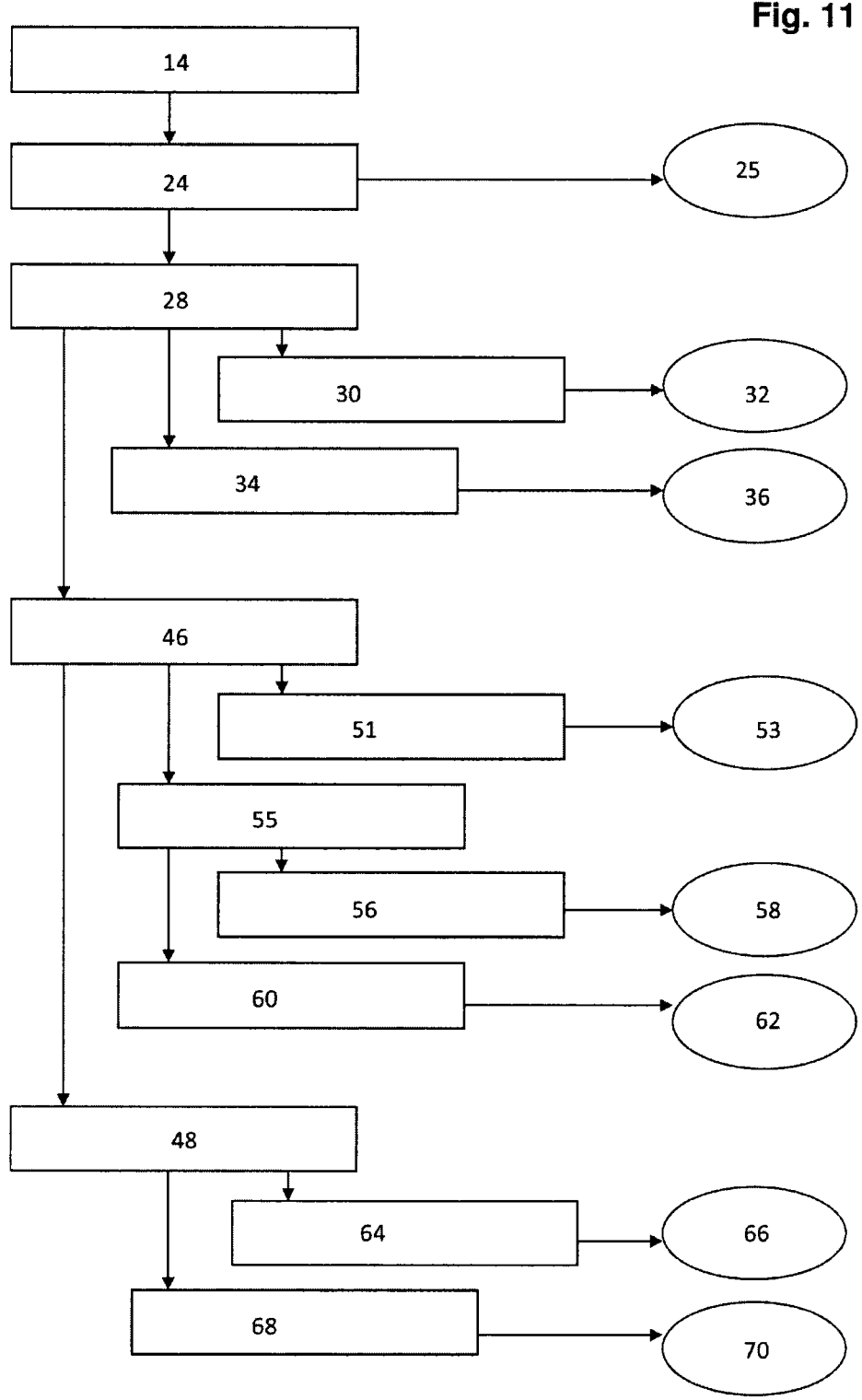
FIG. 11 is a flowchart of the different steps of an embodiment of the method according to the invention.

The present invention proposes a method for analysing a fracture or crack face of a metal part of a turbine engine, in particular made of TiAl, an embodiment of this method being shown schematically by the flowchart in FIG. 11.

A first step 14 of the method from FIG. 11 consists in charting, on a fracture face 10, the cleavage facets using a binocular loupe, that is to say identifying on said face the position and orientation of the cleavage facets. Said cleavage facets show fracture surfaces of fragile grains of the material.

FIG. 4 is an image obtained using a binocular loupe and processed using a computer so as to add arrows which show the position and the orientation of the cleavage facets 16. FIG. 5 is a larger-scale SEM image of a part from FIG. 4. The fracture of the blade from FIG. 4 was obtained by producing a notch 18 in the trailing edge of the blade leaf, then by subjecting the blade to a brutal fracture experiment induced in a laboratory according to a method of bending, from the lower face towards the upper face.

The orientation of the cleavage facets 16 is coherent with the direction of fracture of the blade leaf during bending. The second step 24 of the method from FIG. 11 consists in identifying the initiation region and in determining the direction of fracture (the final fracture region being located opposite the initiation region). This step may also make it possible to determine the geometrical (scratch or impact—reference numeral 25 in FIG. 11) or metallurgical (porosity or inclusion) fault which is the cause of the fracture.

In the example shown in FIG. 4, the cleavage facets 16 are substantially directed from the bottom of the notch 18 (and more specifically perpendicularly to the square corner 20 at the bottom of the notch 18) towards the leading edge 22 of the blade leaf. This makes it possible to locate the initiation of the fracture in the region of said square corner 20 and also to conclude therefrom that said square corner is a geometrical factor in the appearance of the fracture (due to the concentration of stresses in the region of said square corner).

FIG. 6 is an SEM image of another fracture face of a TiAl blade, the fracture having been caused by a high cycle fatigue experiment at ambient temperature. The position and orientation of the cleavage facets 16 make it possible to locate the initiation region 26 in the region of the leading edge of the blade.

TiAl is an alloy which can be used particularly advantageously for a temperature range of from 600 to 800° C. For turbine engine turbines, said alloy is used in low-pressure stages at average temperatures of 750° C. The method according to the invention uses the crystallographic evolution properties of the material according to the temperature to which it is subjected.

Figure 7:
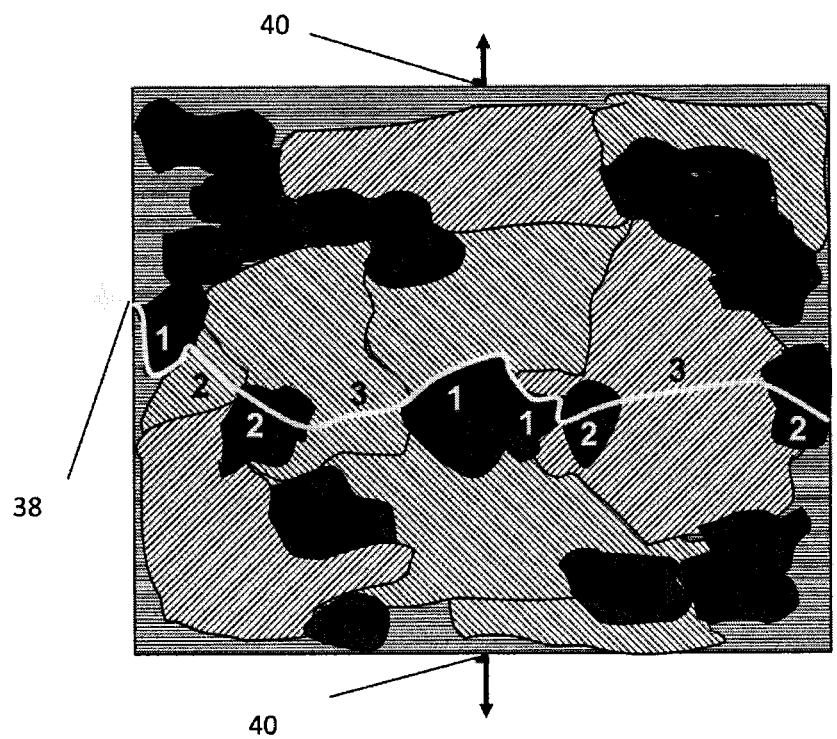
FIG. 7 is a very schematic sectional view of a TiAl part, and shows the progression of a crack through granular regions of the part.
Figure 8:
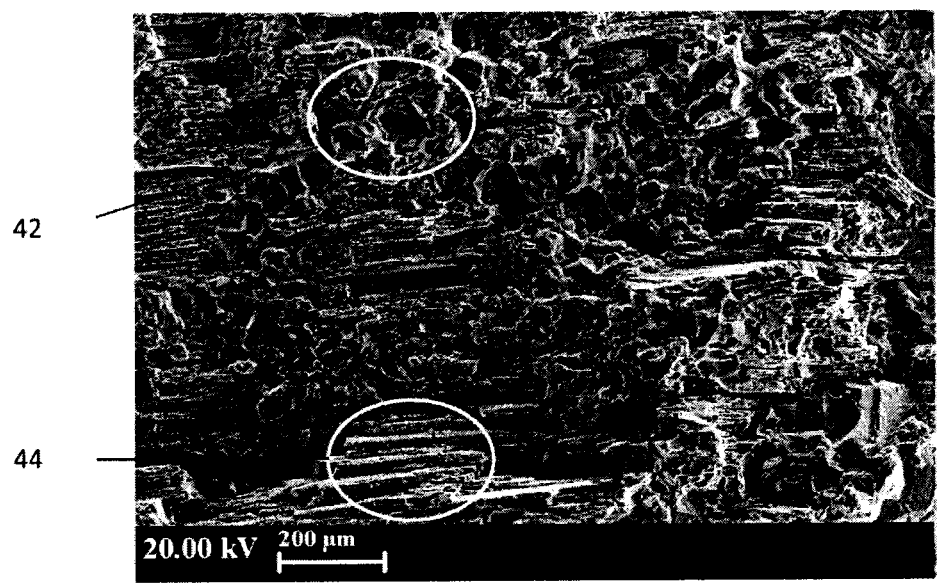
FIG. 8 is a partial SEM image of another fracture face of a TiAl blade, and shows equiaxed grains and lamellar grains.

FIG. 7 is a very schematic sectional view of a TiAl part in which a crack has propagated, the progression of which is indicated by reference numeral 38. Said crack was generated by a pulling experiment (arrows 40) in the sectional plane of the drawing. In this schematic drawing, each region delimited by a continuous line defines a region in which a particular type of grain is present. The grey regions comprise equiaxed grains y and the cross-hatched regions comprise lamellar grains y+α2. The part thus has a duplex microstructure. In addition, the number "1" indicates that the crack has passed around the lamellar grains, which manifests as the presence of intergranular patterns in the surface of the crack face, the number "2" indicates that the crack passes through equiaxed or lamellar grains, which manifests as the presence of cleavage patterns in the surface of the face (the crack propagates in parallel with the lamellae in the case of the lamellar grains), and the number "3" indicates that the crack passes through lamellar grains in a direction which is not in parallel with the lamellae. The propagation of the crack through equiaxed or lamellar grains (reference numerals 2 and 3) leads to the appearance of cleavage facets on the fracture face. The same results are obtained when the part is subjected to a vibratory fatigue experiment at high frequency (HCF) or to an oligocyclic fatigue experiment at low frequency (LCF). Different results were nevertheless obtained according to the temperature of the heat treatment of the part. The equiaxed grains are absent from the fracture surfaces when the part is not exposed to heat. Said grains start to appear above 500° C., and the density thereof increases as the temperature to which the part is exposed increases. A part which is subjected to a heat treatment at 700° C. and is broken at this temperature comprises two to three times more equiaxed grains than a broken part which is subjected to a heat treatment at 500° C. The analysis of the density of equiaxed grains on a fracture or crack face thus also makes it possible to evaluate the temperature experienced by the part.

A third step 28 of the method from FIG. 11 consists in examining an SEM image of the face at the start, in the middle and at the end of fracture. When this examination reveals the presence of intergranular patterns (equiaxed grains—reference numeral 30 in FIG. 11) on the face, this signifies that the crack or fracture took place when hot (that is to say during use—reference numeral 32 in FIG. 11) because these patterns only appear when the material is subjected to a temperature which is greater than 500° C. When the examination reveals a lack of such patterns (reference numeral 34 in FIG. 11), this signifies that the crack or fracture took place when cold (reference numeral 36 in FIG. 11), that is to say during the manufacture of the part.

Due to the appearance of equiaxed grains above 500° C., the presence or absence of said grains in a fracture or crack face makes it possible to determine the temperature level at which the cracking or fracturing takes place. It is thus possible to determine the stage at which cracks appeared, either during manufacture (in the case for example of machining the part at ambient temperature—there are therefore no equiaxed grains in the fracture surface, only cleaved grains), or during operation in the turbine (when hot—it then being relatively easy to differentiate between different grains).

The last steps 46, 48 of the method from FIG. 11 make it possible firstly to determine the temperature level reached by the part and secondly to evaluate the propagation speed of the fracture or crack.

Figure 9:
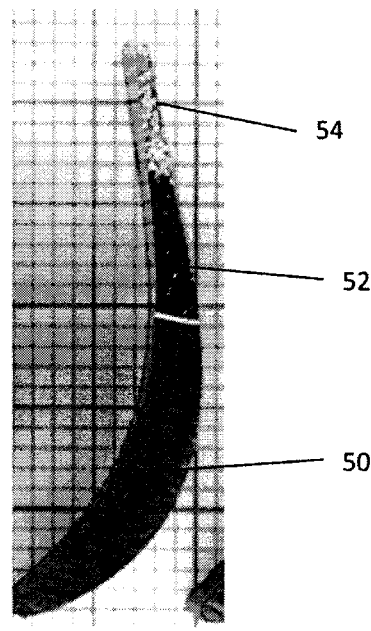
FIG. 9 is a video image of the face of a TiAl blade which has been subjected to an oxidising heat treatment.

FIG. 9 shows the crack face of a blade which has been subjected to an oxidising heat treatment. A notch 50 was made in the leaf of the blade, which was then cracked by a fatigue experiment. The region 52 of the face shows the cracked portion and the region 54 shows a portion which has been cut out after an oxidising heat treatment in order to observe the face. Only the notched portion 50 and the cracked region are coloured because only these portions were exposed to oxidation. This oxidation led to the formation of an oxide layer in the regions 50, 52, which manifests as a superficial heat tint in these regions, this tint being determined by the temperature and the duration of the heat treatment.

A colour chart of the heat tint of the material of the blade is prepared by classifying in said colour chart samples which have been subjected to heat treatments according to the temperature thereof and the duration of the treatment thereof.

For this purpose, a plurality of samples made of a material which is identical to that of the blade are prepared (notched and cracked) and subjected to a heat treatment, as explained above with reference to FIG. 9. In the example in FIG. 10, three sets of samples are prepared, each set comprising six samples, that being a total of eighteen samples.

Said samples are then subjected to different oxidising heat treatments, the heat treatment of each sample being different from the heat treatments of the other samples in terms of the temperature and/or the duration of the treatment thereof. The heat treatments can be carried out by means of an oven into which the samples are introduced, which samples are each equipped with a thermocouple module which is connected to a means which is suitable for measuring the treatment temperature thereof. The oven is supplied with ambient air. The three sets of samples are subjected to treatment temperatures of 600, 700 and 800° C. respectively, and the samples in each set are subjected to treatment durations of 1 minute, 20 minutes, 1 hour, 3 hours, 7 hours and 50 hours respectively.

Superficial heat tints appear on at least some of the samples. Said tints are more or less pronounced and may be quite yellow (Y), ochre (O), brown (Br), blue (Bl), light blue (LB), grey (G) or dark grey (DG). Said tints depend in particular on the nature and the thickness of the oxide layer which forms on the samples during the heat treatment.

Figure 10:
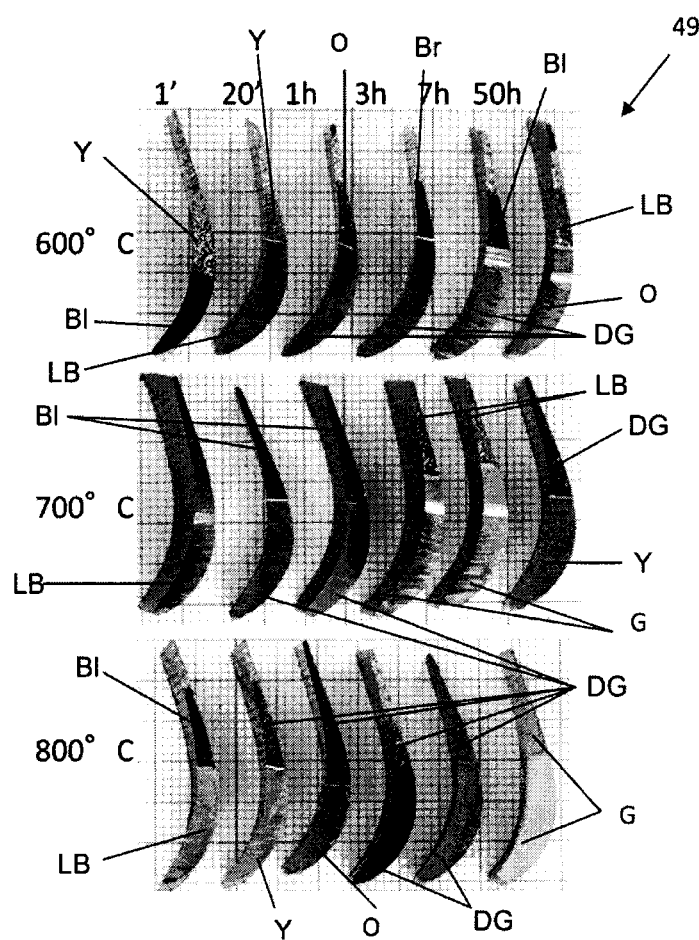
FIG. 10 is a video image of a heat tint colour chart.

FIG. 10 shows a colour chart 49 comprising the above-mentioned eighteen samples, i.e. the three sets of six samples. The samples are fixed to a support to form a table in which each line corresponds to a treatment temperature and each column corresponds to a treatment duration. The treatment temperatures are classified from top to bottom in ascending order and the treatment durations are classified from left to right in ascending order.

The superficial heat hints of the samples have been shown schematically by the letters Y, O, Br, Bl, LB, G and DG, which denote shades of yellow, ochre, brown, blue, light blue, grey and dark grey respectively. When two samples have similar tints, the levels of matteness or shine of these samples may be different and thus make it possible to distinguish between the samples. Moreover, flakes may appear on the surface of the samples. The colour chart clearly reveals that the progression in the superficial heat tint of a part is dependent both on the temperature level reached and on the time for which this temperature is maintained. It is preferable to compare the heat tints of a part directly with the samples from a colour chart and not with photographs of said colour chart because the colours of the samples may be different in the photographs.

Said colour chart firstly makes it possible to determine, from the superficial heat tint of a blade, the temperature level reached by the blade by comparing said tint with those of samples from the colour chart (step 46).

In a first period of time (step 51), the heat tint of the lower face or the upper face of the blade leaf may be compared with those of the samples from the colour chart, so as to evaluate the temperature level 53 reached by the blade.

Then (step 55), the heat tint of the fracture face may be compared with those of the samples from the colour chart. When this tint is uniform 56, it can thus be concluded that the fracture was brutal 58. In the opposite case where the face has a graduated colour 60, it can thus be concluded that the fracture was progressive 62 and is due to fatigue loading.

The colour chart secondly makes it possible to evaluate the propagation speed of the crack or fracture through the heat tint oxidation gradients of the face (step 48). Indeed, in the above-mentioned case where the face has a graduated colour or colour gradient, comparing these tints with those of the samples from the colour chart makes it possible to determine whether the progression of the propagation was rapid 64 or slow 68. A rapid 64 propagation speed signifies that the fracture is due to vibratory fatigue (HCF—66) and a slow propagation speed 68 signifies that it is due to oligocyclic fatigue (LCF—70).

Figure 12:
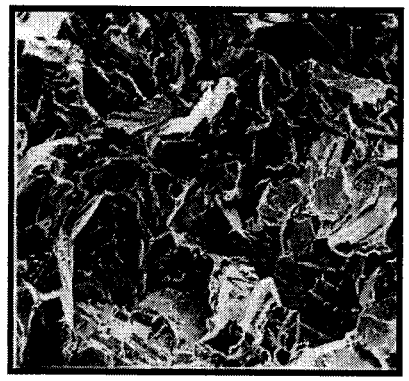
FIGS. 12 to 14 are SEM images of a fracture face showing cleavage facets, equiaxed grains and ductile dimples respectively.
Figure 13:
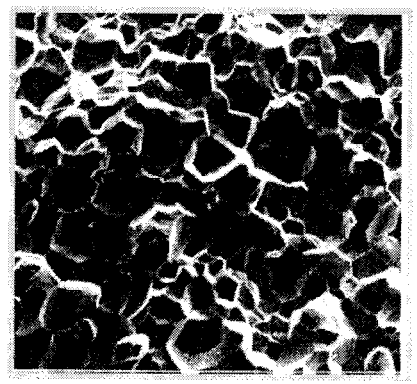
Figure 14:
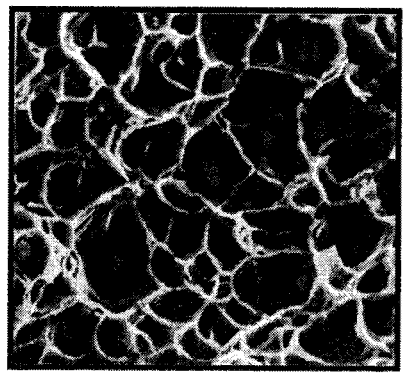

FIGS. 12 to 14 are SEM images of a fracture face showing cleavage facets, equiaxed grains and ductile dimples respectively. The cleavage facets (FIG. 12) and the equiaxed grains (FIG. 13—which appear above 500° C.) which were described above are easy to identify. The ductile dimples (FIG. 14) can also be clearly identified. In theory, said dimples should not appear on fracture faces of TiAl turbine engine parts because said dimples only appear above a temperature of 800° C., and the TiAl turbine engine parts are generally not used at temperatures which are greater than 800° C. However, when said dimples appear on a fracture or crack face of a turbine engine part, this would signify that said part was subjected to abnormal overheating (greater than 800° C.). Analysing the presence of said ductile dimples on the surface of a fracture or crack face thus contributes to the evaluation of the temperature experienced by the part during operation.

The invention claimed is:

1. A method for analyzing a fracture or crack face of a metal part of a turbine engine, said face corresponding to a fracture surface or to a cracking surface before opening in a laboratory for an unbroken cracked part, the method comprising:
   a) identifying on the face a position and orientation of cleavage facets so as to identify an initiation region of the fracture or crack and to determine a direction of propagation of said fracture or crack,
   b) examining the face and detecting regions where at least one of equiaxed grains and lamellar grains are present, so as to evaluate a temperature at which the fracture or crack was made, and
   c) comparing a heat tint of the face with heat tints of samples from a heat tint color chart, said samples being produced from the same material as the part and being subjected to oxidizing heat treatments at predetermined temperatures and for predetermined periods of time, so as to evaluate a speed of propagation of the fracture or crack, steps a), b) and c) being carried out in any order.

2. The method according to claim 1, wherein step a) further includes determining at least one geometrical or metallurgical fault which is able to explain an appearance of the crack or fracture.

3. The method according to claim 1, wherein step a) comprises identifying and directly tracing, in a video image of the face, the position and orientation of the cleavage facets.

4. The method according to claim 1, wherein at least one of steps a) and b) is carried out using at least one of a binocular loupe and a scanning electron microscopy imaging system.

5. The method according to claim 1, wherein step b) further comprises determining whether the fracture or crack took place when hot during use or when cold during manufacture.

6. The method according to claim 1, wherein step b) comprises determining whether the fracture or crack was made above or below 500° C.

7. The method according to claim 1, wherein step b) comprises evaluating the temperature by estimating a density of the equiaxed grains on the face.

8. The method according to claim 1, wherein step b) comprises examining the face and detecting regions where ductile dimples are present.

9. The method according to claim 1, wherein, in step c), before the samples are subjected to heat treatments, a notch is made in each sample which is then subjected to stresses to produce a fracture or crack in a region of said notch.

10. The method according to claim 1, wherein step c) further comprises comparing heat tints on a surface of the part with heat tints of the samples so as to evaluate the temperature level reached by the part.

11. A method for analyzing a fracture or crack face of a metal part of a turbine engine, said face corresponding to a fracture surface or to a cracking surface before opening in a laboratory for an unbroken cracked part, the method comprising:
   a) identifying on the face a position and orientation of cleavage facets so as to identify an initiation region of the fracture or crack and to determine a direction of propagation of said fracture or crack,
   b) examining the face and detecting regions where at least one of equiaxed grains and lamellar grains are present, so as to evaluate a temperature at which the fracture or crack was made, and
   c) comparing a heat tint of the face with heat tints of samples from a heat tint color chart, said samples being produced from the same material as the part and being subjected to oxidizing heat treatments at predetermined temperatures and for predetermined periods of time, so as to evaluate a speed of propagation of the fracture or crack, steps a), b) and c) being carried out in any order,
   wherein step b) further comprises determining whether the fracture or crack took place when hot during use or when cold during manufacture.

* * * * *